United States Patent [19]
Zeiger

[11] Patent Number: 4,888,279
[45] Date of Patent: Dec. 19, 1989

[54] NOVEL IMMUNOSORBENT ASSAYS EMPLOYING ANTIBIOTIC KEYING AGENTS

[75] Inventor: Allen R. Zeiger, Philadelphia, Pa.

[73] Assignee: Thomas Jefferson University, Philadelphia, Pa.

[21] Appl. No.: 243,185

[22] Filed: Sep. 8, 1988

Related U.S. Application Data

[63] Continuation of Ser. No. 684,467, Dec. 21, 1984, abandoned.

[51] Int. Cl.$^4$ ............................................. G01N 33/53
[52] U.S. Cl. ........................................... 435/7; 435/32; 436/501; 436/503; 436/518; 436/531; 436/815; 436/819
[58] Field of Search ...................... 435/7, 32; 436/501, 436/503, 518, 531, 815, 819

[56] References Cited

U.S. PATENT DOCUMENTS

| | | | |
|---|---|---|---|
| 3,852,157 | 12/1974 | Rubenstein | 436/537 |
| 4,446,231 | 5/1984 | Self | 435/7 |
| 4,486,530 | 12/1984 | David | 436/537 |

OTHER PUBLICATIONS

Strominger in β-Lactam Antibiotics, Edited by Salton and Shockman, Academic Press, 1981, pp. 123-125.
Park, H. et al, "Detection of Soluble Peptidoglycan in Urine After Penicillin Administration", *Infection and Immunity*, pp. 139-142, Jan. 1984.
DePedro, M. A. et al., "Affinity Chromatography of Murein Precursors on Vancomycin-Sepharose", *FEMS Microbiology Letters*, 9, pp. 215-217 (1980).
Zeiger, A. R. et al., "Evidence for the Secretion of Soluble Peptidoglycans by Clinical Isolates of *Staphylococcus Aureus*", *Infection and Immunity*, pp. 1112-1118 (Sep. 1982).
Perkins, H., "Specificity of Combination Between Mucopeptide Precursors and Vancomycin or Restocetin", *Journal Biochem*, vol. XXX, pp. 195-205 (1968).
Heymer, B. et al., "A Latex Agglutination Test for Measuring Antibodies ot Streptococcal Mucopeptides", *Journal of Immunology*, vol. 111, No. 2, Aug. 1973, pp. 478-484.
Zeiger, A. et al., "Antibody Levels to Bacterial Peptidoglycan in Human Sera During the Time Course of Endocarditis and Bacteremic Infections Caused by *Staphylococcus Aureus*", *Infection and Immunity*, Sep. 1981, pp. 795-800, vol. 33, No. 3.
Park, H. et al., "Antibodies to Peptiodglycan in Patients with Spondylarthristis: A Clue to Disease Aetiology?", *Annals of Rheumatic Diseases*, vol. 43, pp. 725-728 (1984).
Zeiger, A. et al., "Antibodies Against a Synthetic Peptidoglycan-Precursor Pentapeptide Cross-React with at least Two Distinct Populations of Uncross-Linked Soluble Peptidoglycan Secreted by *Mirococcus luteus* Cells", *Eur. J. Biochem*, vol. 86, pp. 235-240 (1978).
Zeiger, A. et al., "Immunochemistry of a Synthetic Peptidoglycan-Precursor Pentapeptid", *Biochemistry*, vol. 12, No. 18, pp. 3387-3394 (1973).
Heymer, B. et al., "Detection of Antibodies to Bacterial Cell Wall Peptidoglycan in Human Sera", *Journal of Immunology*, vol. 117, No. 1, pp. 23-26, Jul. 1976.
Tynecka, Z. et al., "Peptidoglycan Synthesis in *Bacillus Licheniformis* The Inhibition of Cross-Linking by Benzylpenicillin and Cephaloridine in Vivo Accompanied by the Formation of Soluble Peptidoglycan", *J. Biochem*, vol. 146, pp. 253-267 (1975).
Heymer, B., "Biological Properties of the Peptidoglycan", *Z. Immun—Forsch. Bd.*, vol. 149, pp. 245-257 (1975).
Kegleic, D. et al., "Isolation and Study of the Composition of a Peptidoglycan Complex Excreted by the Biotin-Requiring Mutant of Brevibacterium divaricatum NRRL-2311 in the Presence of Penicillin", *Eur. J. Biochem*, vol. 42, pp. 389-400 (1974).
Rosenthal, R. et al., "Evidence for the Synthesis of Soluble Peptidoglycan Fragments by Protoplasts of *Streptococcus faecalis*", *Journal of Bacteriology*, vol. 124, No. 1, pp. 398-409, Oct. 1975.
Mirelman, D. et al., "Penicillin-Induced Secretion of a Soluble, Uncross-Linked Peptidoglycan by *Micrococcus luteus* Cells", *Biochemistry*, vol. 13, No. 24, pp. 5045-5053 (1974).
Stewart-Tull, D. E. S., "The Immunological Activies of Bacterial Peptidoglycans", *Ann. Rev. Microbiol*, 34:311-40 (1980).
*Methods in Immunology and Immunochemistry*, Edited by Curtis A. Willliams, The Rockefeller University, New York, Academic Press, vol. II, Appendix I, pp. 343-364 (1968).
*Arthritis & Rheumatism*, vol. 21, No. 5 (Jun. 1978).
Ghuysen, J., "Use of Bacteriolytic Enzymes in Determination of Wall Structure and their Role in Cell Metabolism", *Bacteriological Reviews*, pp. 425-565, vol. 32, No. 4, Pt. 2, Dec. 1968.
*The Biologic and Clinical Basis of Infectious Diseases*, Youmans, Paterson & Sommers, 2nd Ed. W. B. Saunders Company, Philadelphia, 1980.

Primary Examiner—Robert Benson
Attorney, Agent, or Firm—Woodcock Washburn Kurtz Mackiewicz & Norris

[57] ABSTRACT

New immunosorbent enzyme assays are provided employing antibiotic keying agents for binding a molecular species to be detected to a test surface followed by binding of an antibody specific for the species and detection of the antibody-species binding. In accordance with preferred embodiments, soluble peptidoglycan is assayed in a fluid binding it to a test surface with vancomycin, reacting the bound material with a peptidoglycan specific antibody, and measuring the extent of the antibody reaction. Assessment of bodily fluids and fermenation broths for the presence of certain kinds of antibiotics is one object of this invention. Assessment of sera for the presence of antibodies that have specificity for soluble peptidoglycans is another object of this invention. Assessment of bodily states in mammals is another object of the invention.

20 Claims, No Drawings

NOVEL IMMUNOSORBENT ASSAYS EMPLOYING ANTIBIOTIC KEYING AGENTS

Portions of this work were supported by Public Health Service grant AI 13525 from the National Institute of Allergy and Infectious Diseases.

This is a continuation of application Ser. No. 684,467, filed Dec. 21, 1984, now abandoned.

FIELD OF THE INVENTION

This invention is directed to improvements in enzyme-linked immunosorbent assays for the improved determination of certain molecular species in liquids either directly or indirectly. More particularly, this invention provides assays for directly measuring the presence of molecular species which are capable of being bound both to an antibody and also to certain antibiotics or other non-immunoglobulins. Particular embodiments are directed to the assay of soluble peptidoglycan, especially in body fluids such as the urine or serum, in an efficient manner with high specificity and precision. This invention provides assays for indirectly measuring the presence of molecular species, examples of which are antibiotics which can cause certain bacteria to secrete soluble peptidoglycans or which can bind to soluble peptidoglycan. This invention also provides assays for measuring the levels of antibodies which have specificity towards soluble peptidoglycans.

BACKGROUND OF THE INVENTION

The detection of biological molecules and the quantification of reaction processes is a central tool of biochemical research. A long-felt need exists for improved methods for the detection of molecular species of biological interest. Such a need exists in particular for the detection of soluble peptidoglycans or of the antibiotics which react with soluble peptidoglycans or with antibodies to soluble peptidoglycans in liquids, especially in bodily fluids or in soil samples, or of antibodies which have specificity towards soluble peptidoglycans.

Peptidoglycans in general have been known to have a variety of biological properties, including the ability to activate the complement system and to stimulate macrophages and lymphocytes. In addition, they are under consideration as possible factors in the origin of some diseases of unknown cause such as systemic rheumatic diseases. Soluble forms of peptidoglycans (SPG) are believed to be murein B lymphocyte activators. A correlation has also been drawn between SPG and certain forms of endocarditis; they may plan a role in other mammalian diseases as well. A sensitive, reliable and specific method for the detection of SPG in biological and other fluids is essential for further medical and biochemical studies. Moreover, general methods for the detection of biological and other molecules are also needed.

Enzyme linked immunosorbent assay (ELISA) has been known heretofore for the detection of antigens. Prior ELISA techniques have bound an antibody from a first species to a surface, which antibody is selectively bindable to the antigen to be detected. The surface-bonded antibody is then contacted by a liquid suspected to contain the antigen. The antigen binds to the surface-bonded antibody, thus, in turn, being bound to the surface. An antibody from a second species, also specific for the antigen to be detected, is then introduced and allowed to bind to the bound antigen. The resulting combination can be referred to as a "sandwich" comprising surface, first antibody, antigen, and second antibody.

An enzymatic system is then attached to or associated with the second antibody in the "sandwich" through a number of techniques. The most common is the use of an enzymatically-labelled antibody from a third species with specificity for the antibody (immunoglobulin) from the second species. The enzymatic system is then provided with substrate and allowed to operate to produce products. The diminution of enzyme substrate or the increase in enzyme products or both is monitored and related to the number of "sandwiches", and hence the number of antigen molecules, which have been bound to the surface.

The ELISA technique suffers from a lack of flexibility. Thus, in order to perform prior ELISA techniques, it is necessary to identify, prepare and isolate two antibodies for each antigen to be detected and to ensure that the two antibodies can bind the antigen simultaneously in the "sandwich". There has been a long-felt need for immunosorbent assays which do not require plural antibodies and which are capable of assaying additional, detectable species with improved efficiency and precision.

Two antibodies may have similarities in their binding sites and thus may bind the same analogues of the natural material to be detected, thereby lowering the specificity and ensuring high backgrounds in the ELISA. Unlike antibodies, antibiotics are not elicited by the natural material to be detected and have a much different binding site for the material. Thus, analogues of the material to be detected that bind to the antibody may well not bind to the antibiotic. Furthermore, plural antibodies from different species may still have some antigenic sites in common. If so, the antibody from the third species may have some specificity to the antibody from the first species, thereby lowering the specificity and ensuring high backgrounds in the ELISA. The antibody from the third species against antibody (immunoglobulin) from the second species is extremely unlikely to cross-react with an antibiotic.

OBJECTS OF THE INVENTION

It is a principal object of the invention to provide assays for molecular species, especially biological species, through immunosorbent techniques.

Another object is to provide improved immunosorbent assays by binding antigen or other detectable species to a surface through binding them to surface-bound antibiotic keying agents.

A further object is to provide novel methods for assaying biological molecules by exploiting their specificity in binding to certain antibiotic species.

Yet another object of the invention is to provide improved methods for detecting and measuring soluble peptidoglycan.

A still further object detects the reaction of a molecular species bound to a surface through the intermediation of an antibiotic keying agent with an antibody specific to the species.

Another object is to provide means for the detection of bodily states in mammals through assaying the presence of molecular species indicative of said states, in body fluids of said mammals.

Another object is to detect the presence of beta-lactam and vancomycin-like antibiotics in bodily fluids and in fermentation broths.

Another object is to detect the presence of antibodies that have specificity towards soluble peptidoglycans.

Further objects will become apparent from a review of the instant specification.

SUMMARY OF THE INVENTION

The present invention provides methods for assaying molecular species in liquids suspected to contain the species either directly or indirectly as a result of the ability of the desired material to cause the appearance of the material to be detected or as a result of the ability of the desired material to cause inhibition of the ELISA which contains a standard quantity of the material to be detected. In accordance with the invention, an antibiotic is attached to a surface and subsequently contacted with the liquid to effect binding of the species to be assayed with the surface-bound antibiotic. The bound species is then reacted with an antibody specific for the species and the extent of the reaction detected to provide the assay. In accordance with preferred embodiments, the detecting step is accomplished by attaching or associating an enzymatic system with reacted antibody and measuring the operation of the enzymatic system.

In accordance with another preferred embodiment, the assay is directed particularly to soluble peptidoglycan. In accordance with this embodiment, the antibiotic is preferably one which is effective against Gram positive bacteria, especially vancomycin or ristocetin, and the selected antibody is one that has been prepared against a peptide having a d-alanyl-d-alanine terminus.

Certain aspects of this embodiment have been described in "Detection of Soluble Peptidoglycan in Urine After Penicillin Administration", Park, Zeiger et al., *Infection and Immunity*, January 1984, pp. 139–142, which is incorporated herein by reference.

Prior immunosorbent assay techniques have employed two antibody species for the detection of a molecular species such as an antigen. In accordance with the present invention, only one antibody is required. Molecular species in a liquid suspected to contain them are assayed by exploiting specificity and binding of certain antibiotics with the specie. Thus, in accordance with the invention, an antibiotic is attached to a surface and is then contacted with the liquid suspected to contain the molecular species to effect binding of the molecular specie to be detected with the antibiotic. The specie to be detected is, accordingly, bound to the surface through the intermediation or "keying" of the antibiotic. The bound specie is then reacted with an antibody specific for the specie to cause the antibody to be bound, in turn, to the surface. A means is then provided for detecting the reaction of the bound molecular specie with the antibody. In accordance with preferred embodiments, an enzymatic system is attached to the antibody, which system is provided with substrate and is placed under conditions sufficient for its operation. The operation of the enzymatic system is then detected through monitoring either the diminution of substrate or the increase in enzyme product or both. Since the enzymatic system can be related quantitatively to the number of assemblages or "sandwiches" present on the surface, the measurement of the enzyme operation can be directly related to the amount of specie to be detected in the liquid.

The invention can also be applied to the detection of antibiotics which cause a sensitive bacterial strain to secrete soluble peptidoglycans. This is done by adding aliquots containing the liquid suspected to contain antibiotic-secreting organisms to the bacterium and incubating the solution with peptidoglycan-precursors and co-factors. This methodology is known to those skilled in the art.

Another instance of the applicability of this invention concerns the renewed interest in discovering natural antibiotics of the beta-lactam and vancomycin classes. The former can be accomplished by adding aliquots from soil fermentation broths to bacteria whose ability to secrete relatively high levels of soluble peptidoglycan is very sensitive to low concentrations of beta-lactam antibiotics. The detection of soluble peptidoglycan would be an indication that an antibiotic-secreting microorganism was present in the fermentation broth. The latter can be accomplished by adding aliquots from soil fermentation broths during the immunosorbent assay at the step in which the antibody is added. Known amounts of soluble peptidoglycan or a synthetic analogue as a substitute will be used in this application of the immunosorbent assay. The inhibition of the immunosorbent assay would be an indication that an antibiotic-secreting microorganism was present in the fermentation broth.

A second instance is the renewed controversy over the use of antibiotics in animals and the subsequent development of antibiotic-resistant enteric bacteria which can cause human disease (refs. on side). The FDA and other government agencies as well as industry will soon have a need of sensitive, specific and reproducible assays for antibiotics in bodily fluids and tissues.

A variation of the ELISA described above can be applied to materials which can bind to only one of the following: antibiotic, soluble peptidoglycan or antibody to peptidoglycan. Such a material can be detected by its ability to cause inhibition of the ELISA, in which a standard quantity of soluble peptidoglycan or a synthetic analogue is used. The reason for this is that the ELISA detects materials that bind to both antibiotic and antibody; i.e., a material that is at least divalent.

Another variation of the ELISA described above can be applied to the detection of antibodies that have specificity towards soluble peptidoglycans, in particular towards the D-alanyl-D-alanine sequence. These antibodies can be detected in unknown sera by their ability to cause the above ELISA to work, in which a standard quantity of soluble peptidoglycan or a synthetic analogue is used and in which the known antibody from the second species specific for the D-alanyl-D-alanine sequence is eliminated. The unknown sera will substitute for the latter.

For the detection of soluble peptidoglycan in accordance with a preferred embodiment of the invention, it has been found that vancomycin can be employed as keying agent to attach soluble peptidoglycan to the testing surface for assay. See Pedro et al., "Affinity Chromatography of Murein Precursors of Vancomycin-Sepharose", *FEMS Microbiology Letters*, 9, Pp. 215–217 (1980); and Perkins "Specificity of Combination Between Mucopeptide Precursors and Vancomycin or Ristocetin", *Biochemistry Journal*, Vol. 11, P. 195 (1969). Thus, the ability of soluble peptidoglycan to bind with specificity both to certain antibodies and to vancomycin type Gram positive antibiotics such as the vancomycins and ristocetins is exploited to provide specific assays for soluble peptidoglycan.

For the antibody to be used for binding to the bound peptidoglycan in accordance with this embodiment, it is preferred to employ an antibody specific to d-alanyl-d-alanine sequence termini proteins, preferably one from an animal source. The sequence is selected in view of its presence in soluble peptidoglycans. Other antibodies may be employed as well so long as it exhibits specificity for SPG. The antibody is prepared in accordance with methods known to those skilled in the art.

As will be apparent from the Examples, a preferred means for detecting the antibody species reaction comprises associating an enzyme system with the reacted antibody, providing substrate for the system and measuring the diminution of substrate or increase in products of the enzyme reaction. This may be conveniently accomplished by employing an intermediate protein for attachment to the antibody, preferably one specific or selectively bindable for proteins from an animalian source of the antibody, and a carrier for enzymes for coupling with the intermediate protein. Methods for determining suitable enzyme systems are also known to those of ordinary skill in the art.

To determine levels of the species to be measured in the fluid it is preferred to compare data gathered from experimental analyses in accordance with the invention with data from analyses of examples having known composition.

EXAMPLES

Vancomycin was purchased from U.S. Biochemical Corp., Cleveland, Ohio; Biotinylated goat anti-rabbit immunoglobulin G (IgG), avidin DH, and biotinylated horseradish peroxidase H were purchased from Vector Laboratories, Inc., Burlington, Calif. The avidin-biotin-horseradish peroxidase complex (ABC) was freshly prepared according to the manufacturer's instructions by adding 50 μl of avidin DH and 50 μl of biotinylated horseradish peroxidase H to 8.0 ml of phosphate-buffered saline, PSB, (pH 7.4) containing 0.5% Tween TM 20 (Sigma Chemical Co., St. Louis, Mo.) and 1% bovine serum albumin (Sigma). O-Phenylenediamine was obtained from Eastman Chemical Co., Rochester, N.Y.

Soluble peptidoglycan, SPG, was obtained from a clinical strain of S. aureus which was incubated for 1 h at 37° C. in a minimal cell wall growth medium containing peptidoglycan precursors and penicillin G (50 μg/ml) as described in "Evidence for the Secretion of Soluble Peptidoglycans by Clinical Isolates of S. aureus", Zeiger et al., Infect. Immunology, Vol. 37, pp. 1112–1118 (1982). The SPG preparation had a high molecular weight (eluted at $V_0$ of Sephadex G-100) and contained peptidoglycan precursor peptide, bound by vancomycin-Sepharose 4B gel. The concentration of SPG was determined by amino acid hydrolysis (6N HCl, 110° C., 16 h). Calculation of the SPG concentration was based on the assumption that all of the muramic acid residues in the glycan were linked to peptide.

The rabbit anti-SPG antibodies were prepared against a synthetic immunogen-containing peptidoglycan precursor pentapeptide (Ala-α-D-Glu-Lys-D-Ala-D-Ala) multiply linked to a random polypeptide carrier. The antibodies were affinity purified by chromatography on a peptidoglycan precursor pentapeptide-Sepharose 4B gel. The concentration of protein was estimated spectrophotomerically using an $E_{280}{}^{1\%}$ of 14.

The tripeptide-t-butoxy-carbonyllysyl-D-alanyl-D-ala-nine (Boc-Lys-D-Ala-D-Ala) was synthesized stepwise by classical chemical coupling procedures.

EXAMPLE 1

A 96-well polyvinyl microtiter plate (Dynatech Laboratories, Alexandria, Va.) was used as the solid-phase carrier. The volume of test materials or reagents added to each well was 0.1 ml. Each washing step consisted of four to five washings with PSB (pH 7.4) containing 0.5% Tween TM 20. Enzyme substrate solutions were freshly prepared by mixing 0.1 ml of 5% $H_2O_2$ and 0.5 ml of o-phenylenediamine (10 mg/ml in methanol) in 50 of 0.1M sodium phosphate buffer (pH 8.0). All other reagents were diluted in PBS-Tween TM -bovine serum albumin just before the assay.

The polyvinyl wells were incubated with vancomycin (100 μg/ml) in carbonate buffer (1.59 g of $Na_2CO_3$, 2.93 g of $NaHCO_3$, 0.2 g of $NaN_3$, in 1 liter of water, pH 9.6) for at least 18 h at 4° C. before use. After washing, each of the samples and standard SPG solutions was placed into four wells, two test wells and two control wells. The plate was incubated in a moist chamber at room temperature for 18 h. After another washing, the wells received reagent mixture containing affinity-purified rabbit anti-SPG (5 μg/ml) and biotinylated anti-rabbit IgG (1:660 dilution), either with the tripeptide inhibitor Boc-Lys-D-Ala-D-Ala (5 μg/ml) for the control wells or without the tripeptide for the test wells. This tripeptide has been shown to be capable of inhibiting antibodies with SPG specificity. The plate was incubated at 37° C. for 2 h. After washing, the ABC complex solution was added to each well. After 1 h of incubation at room temperature, the plate was washed again, and the substrate solution was added, The plate was incubated at room temperature for 1 h in the dark, and the enzyme reaction was stopped by addition of one drop of concentrated $H_2SO_4$ to each well. The entire contents of the wells were transferred to test tubes containing 1.5 ml of deionized water. After vortexing, absorbances were read at 490 nm in a Beckman model 34 spectrophotometer. The mean absorbance values of test and control wells for two determinations were averaged and compared for interpretation. The data are presented in Table 1.

TABLE 1.

| Detectability of SPG in PBS-Tween ® Buffer | | |
|---|---|---|
| | Absorbance at 490 nm | |
| Concentration of SPG (pg/ml) | Test | Control |
| 5,000 | 0.248 | 0.021 |
| 500 | 0.145 | 0.013 |
| 50 | 0.026 | 0.011 |
| 5 | 0.012 | 0.011 |
| 0 | 0.011 | 0.014 |

Ratios of test to control values greater than 2 were considered positive.

EXAMPLE 2

Detectability of SPG added to PBS-Tween TM and Serum

Serial 10-fold dilutions (5 to 5,000 pg/ml) of SPG were made in PSB-Tween TM and a normal human serum containing no detectable antibodies to peptidoglycan. Initial experiments showed a 100-fold difference in detectability of SPG between the serum samples and PBS-Tween TM solutions suggesting the presence of an interfering substance(s) in serum. The following method was devised to remove the interfering substance(s) from serum. One volume of serum was mixed with nine volumes of 5% trichloroacetic by vortexing. The mixture was incubated at room temperature for 20 min and then centrifuged at 1,000 g for 10 min. The supernatant fluid was dialyzed against PBS (pH 7.4) overnight at 4° C. Serial dilutions of SPG in serum were treated as described and then assayed for SPG in accordance with the procedures of Example 1. The data are presented in Table 2.

TABLE 2

Detectability of SPG in Human Serum (Average of Two Determinations)

| Concentration of SPG (pg/ml) | Absorbance at 490 nm | |
|---|---|---|
| | Test | Control |
| 50,000 | 0.263 | 0.030 |
| 5,000 | 0.113 | 0.019 |
| 500 | 0.032 | 0.015 |
| 50 | 0.019 | 0.015 |
| 5 | 0.016 | 0.015 |

EXAMPLE 3

Detection of SPG in Human Sera

Eighty sera from 30 patients with bacterial endocarditis caused by S. aureus, 52 sera from patients with various bacterial infections, and 24 sera from healthy blood donors were assayed for SPG after trichloroacetic acid precipitation. Sera had been collected over several years and stored at −20° C.

EXAMPLE 4

Experiments on Urinary Excretion of SPG After Penicillin Ingestion in Healthy Volunteers Urine specimens were collected at various times of the day from 13 healthy individuals (7 males and 6 females) before and 6 h after oral administration of penicillin VK (250 mg). One individual was given 250 mg of penicillin VK every 6 h for 2 days, and eight sequential posttreatment urine specimens were collected. Both pre- and posttreatment urine specimens were concentrated 20-fold and kept at −70° C. For the SPG assay, the concentrated urine specimens were thawed and mixed with the same volume of PBS-Tween TM. The data are presented in Table 3.

TABLE 3

Study of SPG in Urine Samples Before and After Penicillin Treatment (Average of Two Determinations)

| Subject sex and age (year) | Absorbance at 490 nm | | | |
|---|---|---|---|---|
| | Pretreatment | | Post-treatment | |
| | Test | Control | Test | Control |
| M 41 | 0.010 | 0.009 | 0.043* | 0.011 |
| F 36 | 0.014 | 0.013 | 0.167* | 0.015 |
| F 13 | 0.010 | 0.010 | 0.010* | 0.012 |
| M 40 | 0.009 | 0.010 | 0.013 | 0.012 |
| F 37 | 0.010 | 0.007 | 0.157* | 0.013 |
| F 50 | 0.015 | 0.017 | 0.042* | 0.011 |
| M 36 | 0.012 | 0.012 | 0.009 | 0.011 |
| M 27 | 0.010 | 0.013 | 0.012 | 0.016 |
| F 47 | 0.011 | 0.014 | 0.233* | 0.021 |
| M 34 | 0.013 | 0.012 | 0.013 | 0.012 |
| M 36 | 0.015 | 0.014 | 0.013 | 0.015 |
| F 58 | 0.010 | 0.011 | 0.028* | 0.010 |
| M 26 | 0.007 | 0.009 | 0.008 | 0.009 |

*Considered positive

The detection limit in PBS-Tween TM was 50 pg/ml, whereas the detection limit in serum was 500 pg/ml. The 10-fold difference was as expected from the ten-fold dilution used in the trichloroacetic acid precipitation.

From the detection limits above, only 2 of 80 sera from patients with staphylococcal endocarditis and/or bacteremia were positive. The concentrations of the positive sera were estimated to be in the range of 1 ng/ml. The 52 sera from patients with various bacterial infections and 25 sera from healthy blood donors were all negative.

Six of the six female post-penicillin treatment urine samples, and one of seven male post-treatment samples were positive, whereas all pretreatment samples were negative for SPG (Table 3). Only the first urine sample from the individual given 250-mg doses of penicillin VK every 6 h for 2 days contained detectable SPG. Of the positive urine samples, three had SPG concentrations of greater than 500 pg/ml (or 50 pg/ml in the original specimens if one takes into account the 10-fold concentrations of the specimens before the assay).

What is claimed is:

1. A method for determining the presence of a molecular species in a liquid suspected of containing the species comprising:
    attaching to a surface an antibiotic capable of binding specifically with the molecular species;
    contacting the attached antibiotic with said liquid to effect binding of the species with the antibiotic;
    reacting the bound species with an antibody specific for the species; and reacting the bound antibody with a conjugate of an enzyme and a protein specifically bindable to said bound antibody and measuring the diminution of substrate or the increase in products of the operation of the attached enzyme thereby detecting the presence of said molecular species in said liquid.

2. The method of claim 1 further comprising the step of quantifying the amount of the molecular species in said liquid by relating the amount of bound species to the amount of said molecular species in said liquid.

3. A method for determining the presence of peptidoglycan or synthetic peptidoglycan analog in a liquid suspected of containing the peptidoglycan or peptidoglycan analog comprising:
    attaching to a surface an antibiotic capable of binding specifically with the peptidoglycan or peptidoglycan analog;
    contacting the attached antibiotic with said liquid to effect binding of the peptidoglycan or peptidoglycan analog with the antibiotic;
    reacting the bound peptidoglycan or peptidoglycan analog with an antibody specific for peptidoglycan or peptidoglycan analog; and reacting said bound antibody with a conjugate of an enzyme and a protein specifically bindable to said bound antibody and measuring tnhe diminution of substrate or the increase in products of the operation of the attached enzyme thereby detecting the presence of said peptidoglycan or peptidoglycan analog in said liquid.

4. The method of claim 3 further comprising the step of quantifying the amount of said peptideglycan or peptidoglycan analog in said liquid by relating the amount of bound peptidoglycan or peptidoglycan analog to the amount of said peptidoglycan or peptidoglycan analog in said liquid.

5. The method of claim 3 wherein said fluid is mammalian body fluid.

6. The method of claim 3 wherein said antibiotic is a member of the class of antibiotics effective against Gram positive bacteria.

7. The method of claim 3 wherein the antibiotic is a vancomycin or ristocetin.

8. The method of claim 3 wherein the results of the relating step are compared to the results of the relating steps derived from determinations of known concentrations of peptidoglycan or peptidoglycan analog.

9. The method of claim 3 wherein said antibody is selective for peptide sequences having d-alanyl-d-alanine termini.

10. A method for detecting the presence of beta-lactam antibiotic in a liquid suspected of containing said beta-lactam antibiotic, comprising:
   (a) attaching an antibiotic capable of binding specifically to peptidoglycan or peptidoglycan analog to a surface:
   (b) contacting the attached antibiotic with a known amount of peptidoglycan or peptidoglycan analog to effect binding of said peptidoglycan or peptidoglycan analog to said antibiotic;
   (c) reacting the bound peptidoglycan or peptidoglycan analog at substantially the same time with an antibody specific for peptidoglycan or peptidoglycan analog and an aliquot from said liquid suspected of containing said beta-lactam antibiotic, whereby said antibody and said antibiotic competitively bind to said bound peptidoglycan or peptidoglycan analog; and
   (d) detecting bound antibody specific for peptidoglycan or peptidoglycan analog;
   (e) relating the amount of said antibody reacted with said bound peptidoglycan or peptidoglycan analog to the amount of antibody bound when steps (a)–(d) are performed with a known amount of antibody and the aliquot of liquid suspected of containing said beta-lactam antibiotic is not added, to indicate the amount of beta-lactam antibiotic in said liquid.

11. The method of claim 10 wherein said detecting comprises reacting said bound antibody with a conjugate of an enzyme and a protein specifically bindable to said bound antibody and measuring the diminution of substrate or the increase in products of the operation of the attached enzyme.

12. The method of claim 10 wherein said liquid is soil fermentation broth.

13. The method of claim 10 wherein the antibiotic used in step (a) is a vancomycin or ristocetin.

14. The method of claim 10 wherein said antibody is specific for peptide sequences having d-alanyl-d-alanine termini.

15. A method for detecting peptidoglycan-specific antibodies in body fluid suspected of containing such peptidoglycan-specific antibodies, comprising the steps of:
   attaching to a surface an antibiotic capable of binding specifically to peptidoglycan or peptidoglycan analog;
   containing said attached antibiotic with peptidoglycan or peptidoglycan analog to effect binding of said antibiotic and said peptidoglycan or peptidoglycan analog;
   contacting said bound peptidoglycan or peptidoglycan analog with said body fluid to effect binding of at least a portion of said antibodies present in said body fluid with said bound peptidoglycan or peptidoglycan analog;
   detecting said bound antibody thereby detecting the presence of said antibody in said body fluid.

16. The method of claim 15 further comprising the step of relating the amount of said antibody bound to said peptidoglycan or peptidoglycan analog to results of detecting steps derived from determinations of known quantities of peptidoglycan-specific antibody to determine the amount of said antibody in said body fluid.

17. The method of claim 15 wherein said detecting comprises reacting said bound antibody with a conjugate of an enzyme and a protein specifically bindable to said bound antibody and measuring the diminution of substrate or the increase in products of the operation of the attached enzyme.

18. The method of claim 15 wherein said body fluid is serum.

19. The method of claim 15 wherein the antibiotic is a vancomycin or ristocetin.

20. The method of claim 15 wherein the antibody is specific for peptide sequences having d-alanyl-d-alanine termini.

* * * * *